United States Patent
Mouri et al.

(10) Patent No.: US 10,337,974 B2
(45) Date of Patent: Jul. 2, 2019

(54) PARTICULATE MATTER DETECTION SENSOR

(71) Applicant: DENSO CORPORATION, Kariya, Aichi-pref. (JP)

(72) Inventors: Tomotaka Mouri, Kariya (JP); Masayuki Tamura, Kariya (JP); Masahiro Yamamoto, Kariya (JP); Go Miyagawa, Kariya (JP); Hironobu Shimokawa, Nishio (JP); Kazuhiko Koike, Nishio (JP)

(73) Assignee: DENSO CORPORATION, Kariya (JP)

( * ) Notice: Subject to any disclaimer, the term of this patent is extended or adjusted under 35 U.S.C. 154(b) by 66 days.

(21) Appl. No.: 15/569,510

(22) PCT Filed: Apr. 12, 2016

(86) PCT No.: PCT/JP2016/061749
§ 371 (c)(1),
(2) Date: Oct. 26, 2017

(87) PCT Pub. No.: WO2016/175022
PCT Pub. Date: Nov. 3, 2016

(65) Prior Publication Data
US 2018/0266934 A1    Sep. 20, 2018

(30) Foreign Application Priority Data
Apr. 28, 2015   (JP) ................................. 2015-091242

(51) Int. Cl.
*G01M 15/10*    (2006.01)
*G01N 15/00*    (2006.01)
*G01N 15/06*    (2006.01)

(52) U.S. Cl.
CPC ...... *G01N 15/0656* (2013.01); *G01M 15/102* (2013.01); *G01N 15/0606* (2013.01); *G01N 2015/0046* (2013.01)

(58) Field of Classification Search
CPC ............ F01N 2560/05; G01N 15/0606; G01N 2015/0046; G01N 1/2252; G01N 27/4071
See application file for complete search history.

(56) References Cited

U.S. PATENT DOCUMENTS 4,656,832 A * 4/1987 Yukihisa ................. F01N 3/027
                                                                    324/717
8,176,768 B2 * 5/2012 Kondo ............... G01N 15/0656
                                                                     73/23.33
(Continued)

FOREIGN PATENT DOCUMENTS

DE    10 2006 047 927    4/2008
JP         59-197847    11/1984
(Continued)

OTHER PUBLICATIONS

International Search Report issued in corresponding Japanese Application No. PCT/JP2016/061749 (1 page), dated Jun. 21, 2016.

*Primary Examiner* — David A Rogers
(74) *Attorney, Agent, or Firm* — Nixon & Vanderhye P.C.

(57) ABSTRACT

A particulate matter detection sensor has an element part for detecting an amount of PM contained in exhaust gas emitted from an internal combustion engine. A deposition part and at least a pair of detection electrodes are formed on an end surface of the element part. Some of particles of PM is deposited on the deposition part. The pair of detection electrodes are arranged on the deposition part. The particulate matter detection sensor changes its output electrical signal according to variation of electrical properties between the pair of the detection electrodes due to deposition of PM on the deposition part. A concave collection part is formed (Continued)

on the deposition part. The concave collection part has a concaved shape when viewed from the edge surface of the element part.

9 Claims, 6 Drawing Sheets

(56) References Cited

U.S. PATENT DOCUMENTS

| | | | | |
|---|---|---|---|---|
| 9,206,757 | B2* | 12/2015 | Matuoka | F02D 41/1466 |
| 9,523,632 | B2* | 12/2016 | Nishijima | G01N 15/0656 |
| 2001/0051108 | A1* | 12/2001 | Schonauer | G01N 25/22 |
| | | | | 422/68.1 |
| 2003/0196499 | A1* | 10/2003 | Bosch | G01N 15/0656 |
| | | | | 73/865.5 |
| 2004/0244472 | A1* | 12/2004 | Nakamura | G01N 27/4077 |
| | | | | 73/114.75 |
| 2008/0314748 | A1* | 12/2008 | Yamauchi | G01N 27/4067 |
| | | | | 204/431 |
| 2009/0126458 | A1* | 5/2009 | Fleischer | G01N 15/0656 |
| | | | | 73/28.01 |
| 2009/0217737 | A1* | 9/2009 | Dorfmueller | F01N 11/00 |
| | | | | 73/28.01 |
| 2010/0000404 | A1* | 1/2010 | Sakuma | G01N 15/0656 |
| | | | | 95/3 |
| 2010/0000863 | A1* | 1/2010 | Kondo | G01N 15/0656 |
| | | | | 204/406 |
| 2010/0312488 | A1* | 12/2010 | Diehl | G01N 15/0656 |
| | | | | 702/23 |
| 2011/0081276 | A1* | 4/2011 | Teranishi | F23N 5/003 |
| | | | | 422/83 |
| 2011/0156727 | A1* | 6/2011 | Achhammer | F02D 41/1466 |
| | | | | 324/691 |
| 2012/0055233 | A1* | 3/2012 | Kondo | G01N 15/0656 |
| | | | | 73/28.02 |
| 2012/0186330 | A1 | 7/2012 | Ueno et al. | |
| 2013/0283886 | A1* | 10/2013 | Teranishi | G01N 33/0047 |
| | | | | 73/23.31 |
| 2013/0298640 | A1* | 11/2013 | Ante | F02D 41/1466 |
| | | | | 73/28.01 |
| 2014/0223887 | A1* | 8/2014 | Duault | F01N 9/002 |
| | | | | 60/274 |
| 2014/0238108 | A1* | 8/2014 | Di Miro | G01N 27/04 |
| | | | | 73/28.01 |
| 2014/0245815 | A1* | 9/2014 | Nishijima | G01N 15/0656 |
| | | | | 73/23.31 |
| 2014/0311129 | A1* | 10/2014 | Hashida | F02D 41/1466 |
| | | | | 60/274 |
| 2014/0326064 | A1* | 11/2014 | Nakano | G01F 1/6842 |
| | | | | 73/204.26 |
| 2015/0177204 | A1* | 6/2015 | Bessen | G01N 15/0656 |
| | | | | 73/1.06 |
| 2016/0334321 | A1* | 11/2016 | Koike | G01N 15/0606 |
| 2017/0131185 | A1* | 5/2017 | Koike | G01N 27/04 |
| 2017/0146440 | A1* | 5/2017 | Zhang | G01N 15/0606 |
| 2017/0160179 | A1* | 6/2017 | Kim | G01M 15/102 |
| 2017/0168002 | A1* | 6/2017 | Yang | F01N 11/00 |
| 2017/0261463 | A1* | 9/2017 | Sugiura | G01N 27/4071 |
| 2017/0315042 | A1* | 11/2017 | Miyagawa | G01N 27/04 |
| 2017/0322134 | A1* | 11/2017 | Koike | G01N 15/06 |
| 2017/0350300 | A1* | 12/2017 | Koike | F01N 3/00 |
| 2017/0363530 | A1* | 12/2017 | Asmus | G01N 27/043 |
| 2018/0266936 | A1* | 9/2018 | Yamamoto | G01N 27/045 |
| 2018/0328832 | A1* | 11/2018 | Asmus | F02D 41/1466 |
| 2019/0033195 | A1* | 1/2019 | Miyagawa | G01N 15/0656 |

FOREIGN PATENT DOCUMENTS

| | | |
|---|---|---|
| JP | 60-196659 | 10/1985 |
| JP | 2012-078130 | 4/2012 |

* cited by examiner

FIG.6 ably an adequate detection sensitivity of the particulate matter detection sensor. As a result, the conventional structure reduces a detection sensitivity of the particulate matter detection sensor, and it is difficult for the particulate matter detection sensor to have an adequate detection sensitivity.

PARTICULATE MATTER DETECTION SENSOR

This application is the U.S. national phase of International Application No. PCT/JP2016/061749 filed Apr. 12, 2016 which designated the U.S. and claims priority to JP Patent Application No. 2015-091242 filed Apr. 28, 2015, the entire contents of each of which are hereby incorporated by reference.

The present invention has been made in consideration of the foregoing circumstances, and it is an object of the present invention to provide a particulate matter detection sensor having an improved structure capable of increasing a detection sensitivity to detect particulate matter contained in exhaust gas.

TECHNICAL FIELD

The present invention relates to particulate matter detection sensors capable of detecting amount of particulate matter contained in exhaust gas.

Solution to Problem

In accordance with one aspect of the present invention, there is provided a particulate matter detection sensor having an element part, a deposition part, and at least a pair of detection electrodes. The element part detects an amount of particulate matter contained in exhaust gas emitted from an internal combustion engine. The deposition part is formed in the element part, and capable of collecting some of the particulate matter contained in exhaust gas. The pair of detection electrodes are formed on the deposition part. The pair of detection electrodes face with each other at a predetermined interval. The particulate matter detection sensor is configured to change an output electrical signal due to electrical properties between the pair of the detection electrodes when the particulate matter are deposited on the deposition part. The deposition part has a concave collection part formed in a concave shape. The concave collection part has a pair of a first detection surface and a second detection surface arranged adjacently with each other in an adjacent direction. The adjacent direction is perpendicular to a depth direction of the concave collection. A component of a normal vector of each of the first detection surface and the second direction surface in the adjacent direction is in a reverse direction with each other. When observed from the depth direction of the concave collection part, each of the pair of detection electrodes extends from the first detection surface toward the second detection surface along the adjacent direction. The pair of detection electrodes are arranged to face with each other in an orthogonal direction which is perpendicular to the adjacent direction and the depth direction.

BACKGROUND ART

In general, an exhaust gas purification device is mounted to an exhaust gas pipe of an internal combustion engine. The exhaust gas purification device traps and collects particulate matter (PM) contained in exhaust gas. The exhaust gas purification device has a particulate matter detection sensor capable of detecting an amount of PM contained in exhaust gas. In order to detect failure of the exhaust gas purification device, a detection process is performed based on information of the detection results regarding the amount of PM transmitted from the particulate matter detection sensor.

For example, patent document 1 shows a particulate matter detection sensor to be used in such an exhaust gas purification device. The particulate matter detection sensor of the patent document 1 has a substrate, and detection electrodes formed on a surface of the substrate. The substrate has is electrically insulating. A plurality of protruding parts are formed on the substrate so as to cover the electrodes.

CITATION LIST

Patent Literature

[Patent document 1] German patent laid open publication No. DE 102006047927.

SUMMARY OF INVENTION

Technical Problem

However, the particulate matter detection sensor shown in the patent document 1 previously described has following drawbacks. When exhaust gas emitted from an internal combustion engine reaches the particulate matter detection sensor, particles of particulate matter (PM) collide with each other on the substrate of the particulate matter detection sensor, and the particulate matter detection sensor traps and collects some particles of particulate matter. However, when such particles of particulate matter move at a high speed, some particles of particulate matter collides with the surface of the substrate, and rebound from the surface of the substrate without deposited by the particulate matter detection sensor. In particular, on the protruding parts formed on the substrate, it is difficult to provide a voltage to be used for collecting particles of PM because a distance between the surface of the protruding parts and the detection electrodes is long, and the particles of particulate matter easily rebound from the surface of the substrate. This conventional structure reduces a collection rate of particles of particulate matter In accordance with another aspect of the present invention, there is provided a particulate matter detection sensor having an element part capable of detecting an amount of particulate matter contained in exhaust gas emitted from an internal combustion engine. The element part has a deposition part, at least a pair of detection electrodes and a laminated part. The deposition part and the pair of detection electrodes are formed on at least one surface of the element part. The deposition part collects some of the particulate matter contained in exhaust gas. The pair of detection electrodes are arranged on the deposition part. The particulate matter detection sensor generates and transmits an output electrical signal which is changed due to electrical properties between the pair of the detection electrodes. The electrical properties between the pair of the detection electrodes are changed due to the amount of particulate matter deposited on the deposition part. The deposition part has a concave collection part. The concave collection part has a concave shape when viewed from one surface of the element part. In the laminated part, a plurality of the detection electrodes and a plurality of lamination members are electrically insulating are alternately stacked. The deposition part and the plurality of the detection electrodes are formed on an edge surface of the laminated part.

Advantageous Effects of Invention

Because the particulate matter detection sensor having the structure previously described has the concave collection part, this structure makes it possible to trap and collect particulate matter which has collided with the deposition part with high efficiency. When particulate matter enters in the inside of the concave collection part collides with an inner peripheral part of the concave collection part, and rebounds from the inner peripheral part of the concave collection part, the rebounded particulate matter easily collides again with the inner peripheral part of the concave collection part because the concave collection part is formed to cover the element part when viewed from the one surface of the element part. At this time, because the moving speed of the particulate matter is reduced after the particulate matter collides with the concave collection part at the first collision, the rebounded particulate matter has a reduced moving speed, and easily deposited onto the inner peripheral part of the concave collection part. This structure of the particulate matter detection sensor having the concave collection part makes it possible to increase the collection rate of particles of particulate matter.

As previously described, it is possible for the present invention to provide the particulate matter detection sensor having an increased excellent detection sensitivity to detect particulate matter contained in exhaust gas.

DESCRIPTION OF EMBODIMENTS

The particulate matter detection sensor according to the present invention has the detection electrodes. The detection electrodes have an outer electrode part and an inner electrode part. The outer electrode part is formed at the outside part of the concave collection part. The inner electrode part is formed at the inside part of the concave collection part. It is preferable for the outer electrode part and the inner electrode part to be electrically connected together on the surface of the element part. This structure makes it possible to detect particulate matter contained in exhaust gas at the outside of the concave collection part, to increase the probability of colliding again with the deposition part, and to increase the collection rate of the deposition part because the inner electrode part are formed in the concave collection part having a high collection rate of particles of particulate matter. As a result, this structure makes it possible to improve the detection sensitivity of the particulate matter detection sensor.

The particulate matter detection sensor has a protection cover which covers the deposition part and elements around the deposition part. The protection cover has gas inlet holes so as to introduce exhaust gas into the inside of the element part. It is preferable for the particulate matter detection sensor to have the structure capable of generating the flow of exhaust gas, which has been introduced through the inlet holes, to the concave collection part. This structure of the particulate matter detection sensor makes it possible to supply exhaust gas containing particulate matter to the deposition part with high efficiency. Further, because this structure uniquely generates the flow of exhaust gas to the deposition part and the deposition part is formed on the generated flow of exhaust gas, this structure makes it possible to further improve the collection rate of the deposition part having the concave collection part.

In addition, it is preferable for the surface of the concave collection part to have a bowl shape having an arc-shaped cross section which is perpendicular to the arrangement of the pair of the detection electrodes. Because an angle of the inner peripheral part of the concave collection part having a bowl shape having an arc-shaped curved surface is gradually changed, this structure allows the particulate matter to fly and move in plural directions and to collide with the concave collection par. As a result, this structure allows the concave collection part to collect particulate matter with high efficiency.

Further, it is preferable for the particulate matter detection sensor to have plural concave collection parts. This structure makes it possible to increase a total amount of deposited particulate matter on the plural concave collection parts. Accordingly, this structure increases the collection rate of the particulate matter detection sensor, and provides the particulate matter detection sensor having the improved detection sensitivity.

EXEMPLARY EMBODIMENTS

First Exemplary Embodiment

Figure 1:
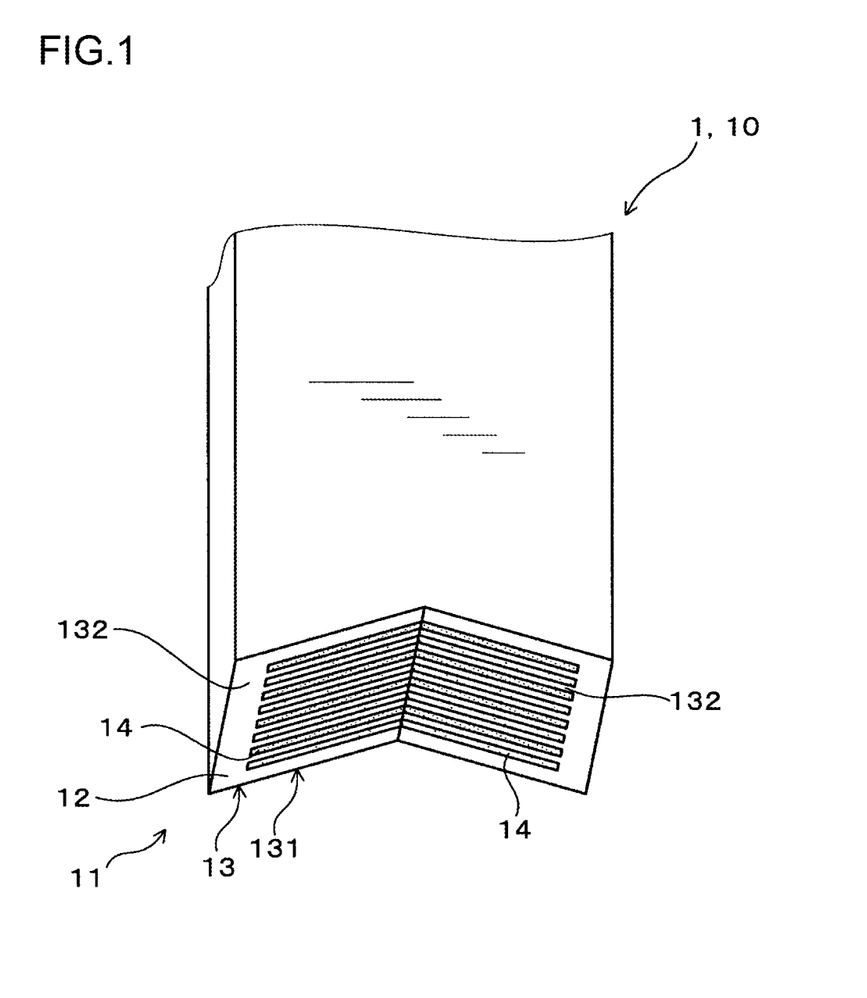
FIG. 1 is a schematic view explaining an element part of a particulate matter detection sensor according to a first exemplary embodiment of the present invention.

A description will be given of the particulate matter detection sensor according to the first exemplary embodiment with reference to FIG. 1 to FIG. 4. As shown in FIG. 1, the particulate matter detection sensor 1 has an element part 10 capable of detecting an amount of particulate matter contained in exhaust gas emitted from an internal combustion engine. The element part 10 has a deposition part 13 and a pair of detection electrode 14 which are formed at a front surface of the element part 10. Some of particulate matter is accumulated, i.e. deposited on the deposition part 13. The pair of detection electrode 14 are arranged on the deposition part 13. The particulate matter detection sensor 1 is configured to vary an output electrical signal on the basis of change of electric properties between the pair of the detection electrodes 14 due to the accumulation of particulate matter on the deposition part 13. As shown in FIG. 1, a concave collection part 131 is formed on the deposition part 13

Hereinafter, a more detailed description will be given of the structure and action of the particulate matter detection sensor 1 according to the first exemplary embodiment. The particulate matter detection sensor 1 according to the first exemplary embodiment is used for detecting particulate matter contained in exhaust gas emitted from an internal combustion engine of a motor vehicle. The exhaust gas is discharged to the outside of the motor vehicle through an exhaust gas pipe. Failure detection of an exhaust gas purification device is performed on the basis of information transmitted from the particulate matter detection sensor 1.

Figure 4:
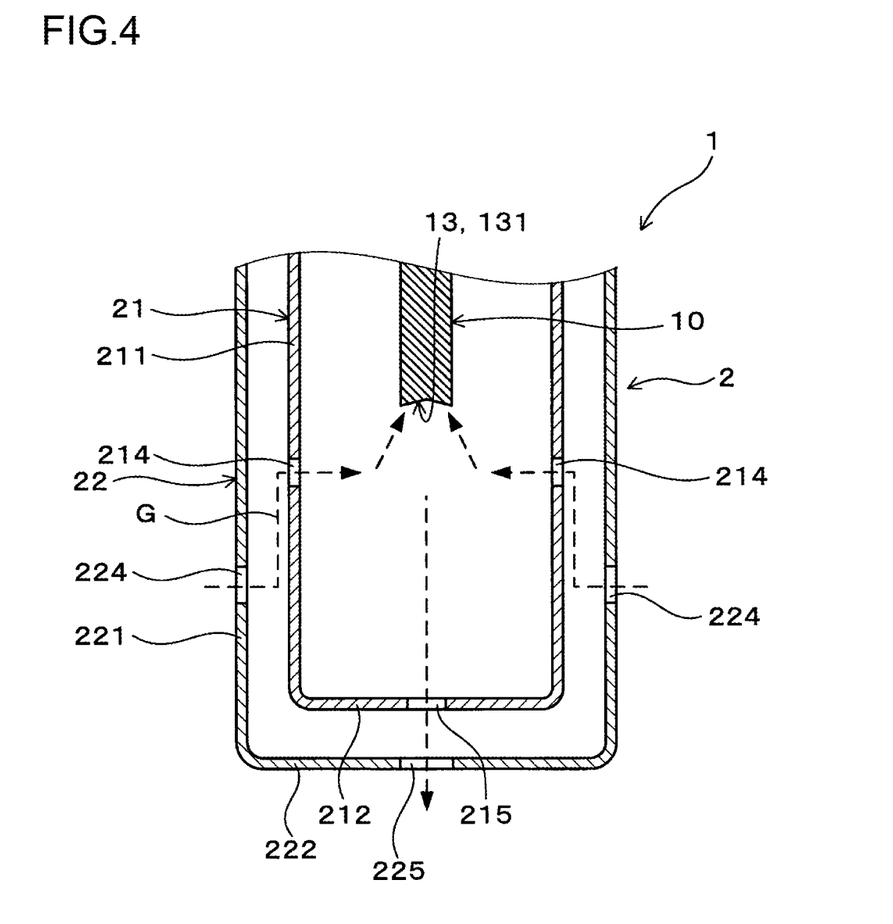
FIG. 4 is a view showing a cross section of the particulate matter detection sensor according to the first exemplary embodiment of the present invention.

As shown in FIG. 4, the particulate matter detection sensor 1 has the element part 10, a protection cover 2 and a housing member (not shown). The housing case supports the element part 10 and the protection cover 2.

Figure 2:
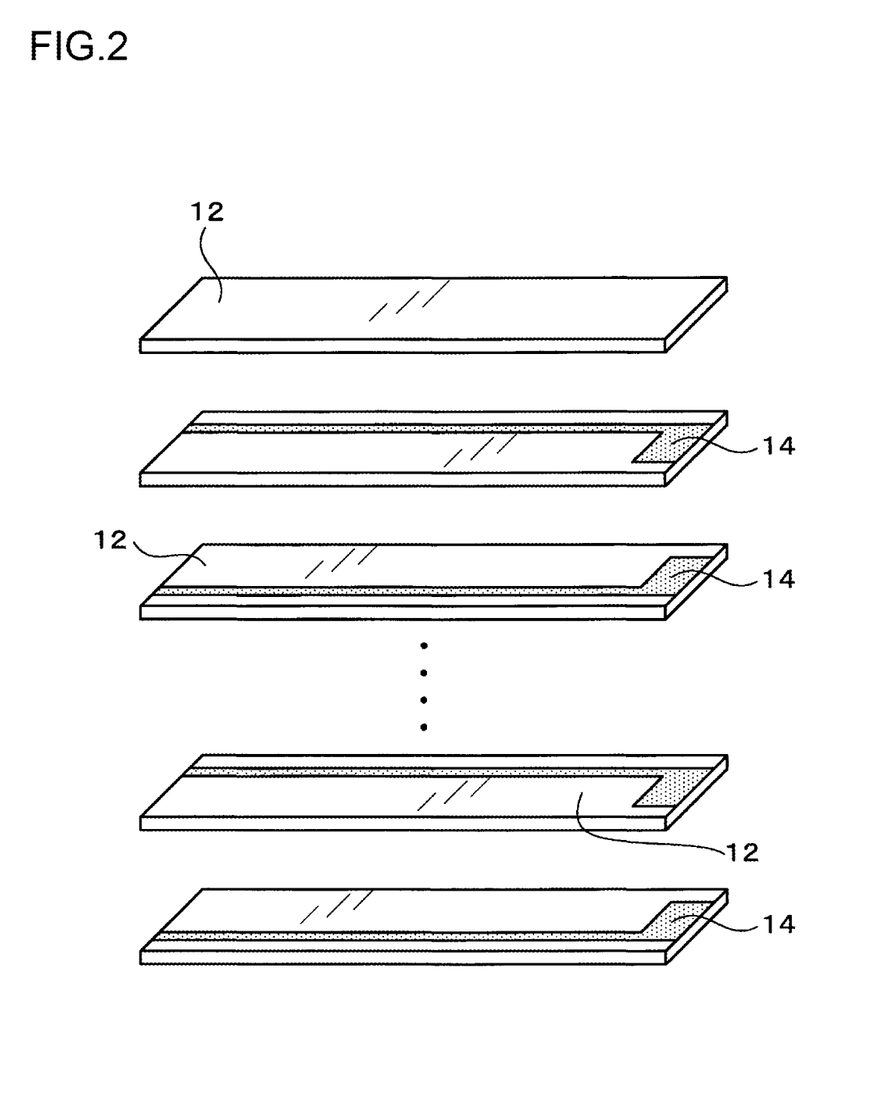
FIG. 2 is a view explaining a structure of the element part of the particulate matter detection sensor according to the first exemplary embodiment of the present invention.

As shown in FIG. 2 and FIG. 4, the element part 10 approximately has a rod shape, the deposition part 13 is formed on a front surface of the element part 10. Particulate matter contained in exhaust gas is accumulated on the deposition part 13. The deposition part 13 has nine insulation members 12 and eight detection electrode parts in the pair of the detection electrodes 14. The eight detection electrode parts are arranged between the nine insulation members 12, respectively. However, the present invention does not limit the number of the nine insulation members 12 and the number of the eight detection electrode parts in the pair of the detection electrodes 14. For example, it is acceptable to have not less than two detection electrode parts. Further, it is acceptable to have the insulation members 12, wherein the number of the insulation members is more than the number of the detection electrode parts+1. When plural pairs of the detection electrodes 14 are arranged, the particulate matter detection sensor 1 provides an output current which is the total sum of each of the plural pair of the detection electrodes. Accordingly, the more the number of the detection electrodes 14, the higher the detection sensitivity of the particulate matter detection sensor 1.

Figure 3:
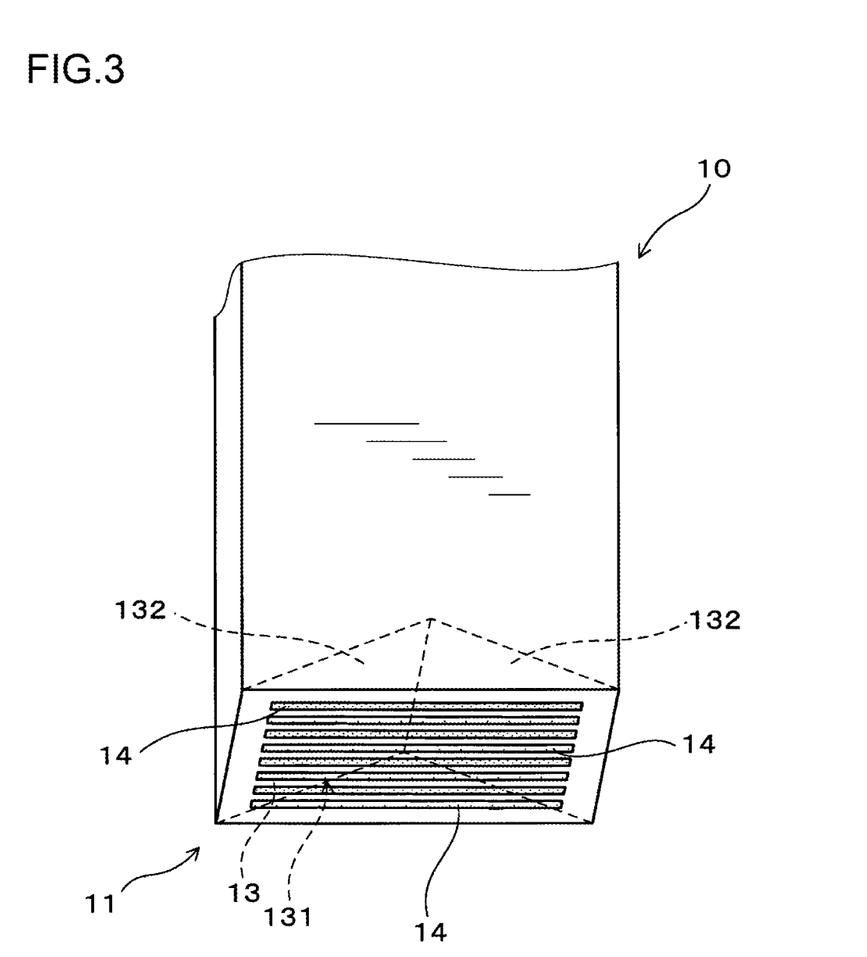
FIG. 3 is a view explaining a structure of a spare part of the particulate matter detection sensor according to the first exemplary embodiment of the present invention.

As shown in FIG. 2 and FIG. 3, the insulation member 12 has a plate shape and is made of ceramic materials composed of alumina, zirconia, magnesia, beryllia, etc. The detection electrodes 14 are produced by using screen printing using conductive paste such as platinum paste, copper paste, silver paste, etc. It is acceptable to use gravure printing, inkjet printing, etc. instead of using such screen printing so as to form a pattern of the detection electrodes.

the insulation members 12, on which the detection electrode have been formed, are stacked to make a lamination, and fired to produce a laminated part 11 in which the insulation members 12 and the detection electrode parts are alternately stacked.

The present invention does not limit the method of producing the laminated part 11. It is acceptable to use the following method. That is, the plural detection electrode parts are formed on the insulation member having a size of including the plural insulation members 12. The insulation members on which the plural detection electrode parts are formed are stacked, and cut into plural pieces by a cutting process. Finally, each of the pieces is fired to produce the laminated part 11. The latter method reduces the total number of steps to produce plural particulate matter detection sensors.

A positive electrode and a negative electrode are alternately arranged on the laminated part 11 so as to provide the detection electrode parts which are adjacently with each other. That is, each pair of the detection electrode parts, which are arranged alternately with each other, forms a pair of the detection electrodes 14. The deposition part 13 is formed on the front surface when viewed in an axial direction of the particulate matter detection sensor 1. The deposition part 13 is exposed around the edge part of the detection electrodes 14.

Further, the concave collection part 131 is formed on the deposition part 13 at the front surface of the particulate matter detection sensor 1. The concave collection part 131 has a concave shape when viewed from the front end surface of the particulate matter detection sensor 1. The concave collection part 131 is composed of two inclined surfaces 132. The two inclined surfaces 132 are inclined approximately toward the direction of the distal end part of the particulate matter detection sensor 1, i.e. approximately inclined in the direction which is perpendicular to the lamination direction in the laminated part 11 and is also perpendicular to the axial direction of the particulate matter detection sensor 1. The detection electrodes 14 are exposed on the two inclined surfaces 132. As shown in FIG. 3, in the particulate matter detection sensor 1 according to the first exemplary embodiment, the concave collection part 131 is formed by a cutting process after the insulation members 12 have been fired.

The present invention does not limit the process of forming the concave collection part 131 previously described. For example, it is possible to use a punching process for punching the insulation member 12 or a cutting process for cutting the insulation member 12, where the detection electrodes 14 have been formed on the insulation member 12 before forming the lamination. After forming the lamination, it is acceptable to use a cutting process or a machining process of processing the lamination so as to form the concave collection part 131 before the firing process.

It is preferable to form the lamination after the firing process. This makes it possible to simultaneously correct a surface waviness and a distortion of the concave collection part 131 due to a shrinkage between the insulation member 12 and the detection electrodes 14 during the firing process.

In the particulate matter detection sensor 1 according to the first exemplary embodiment having the structure previously described, when a collection voltage is applied to the detection electrodes 14 formed on the deposition part 13, an electric field is generated around the detection electrodes 14, and some particles of particulate matter is attracted to the detection electrodes 14. The particles of particulate matter adhered on the detection electrodes 14 move on the surface of the detection electrodes 14, and accumulate on the deposition part 13 between the pair of the detection electrodes 14. An electric conduction is generated between the pair of the detection electrodes 14 exposed on the deposition part 13 by the particles of particulate matter accumulated on the deposition part 13, and an electric resistance between the pair of the detection electrodes 14 is reduced. A current value as an electric signal which flows between the detection electrodes 14 varies due to the variation of the electric resistance between the detection electrodes 14. This varies the current value output from the particulate matter detection sensor 1. That is, the current value provided from the particulate matter detection sensor 1 varies according to the variation of the amount of particulate matter accumulated on the deposition part 13. That is, the current value of the particulate matter detection sensor 1 represents information regarding the amount of particulate matter accumulated on the deposition part 13. It is possible to detect the amount of particulate matter accumulated on the deposition part 13 on the basis of the current value of the particulate matter detection sensor 1.

In the particulate matter detection sensor 1 according to the first exemplary embodiment, the current value of the element part 10 is supplied to a control unit (not shown) having a shunt resistance. The control unit multiplies the obtained current value and a value of the shunt resistance to obtain a voltage. The particulate matter detection sensor 1 transmits this output voltage.

As shown in FIG. 4, the protection cover 2 has an inside cover 21 and an outside cover 22. The outside cover 22 is arranged at the outer peripheral side. The inside cover 21 has an inside wall part 211 and an inside bottom part 212. The inside wall part 211 has a cylindrical shape, and accommodates the element part 10. The inside bottom part 212 is formed at a front end of the inside wall part 211. The inside cover 21 is fixed to the front surface of the housing member (not shown) by caulking.

Inside introduction holes 214 are formed in the inside wall part 211. Each of the inside introduction holes 214 has a circular shape. When viewed in the axial direction of the protection cover 2, the inside introduction holes 214 are arranged at a regular interval in the circumferential direction of the inside wall part 211. The inside introduction holes 214 are formed further towards the front side than the deposition part 13 in the element part 10.

An inside exhaust hole 215 is a through hole formed at the central portion of the inside bottom part 212 in the axial direction of the protection cover 2.

The outside cover 22 has an outside wall part 221 of a cylindrical shape which surrounds the protection cover 2, and an outside bottom part 222 formed at a front end part of the outside wall part 221. The outside cover 22 and the inside cover 21 is fixed to the front end surface of the housing member by caulking.

An outside introduction holes 224 are formed in the outside wall part 221. Each of the outside introduction holes 224 has a circular shape. When viewed in the axial direction of the protection cover 2, the outside introduction holes 224 are arranged at a regular interval in the circumferential direction of the outside wall part 221. Each of the outside introduction holes 224 and each of the inside introduction holes 214 are at corresponding positions, respectively in the radial direction of the protection cover 2. The outside introduction holes 224 are arranged toward the front end side of the protection cover 2 when compared with the position of the inside introduction holes 214. An outside exhaust hole 225 is a through hole formed at the central portion of the outside bottom part 222 in the axial direction of the protection cover 2.

In the particulate matter detection sensor 1 according to the first exemplary embodiment, the flowing direction of the exhaust gas G is changed after the exhaust gas G is introduced into the inside of the particulate matter detection sensor 1 through the outside introduction holes 224. The exhaust gas G is then introduced into the inside of the inside cover 21 through the inside introduction holes 214. That is, the exhaust gas G flowing in the exhaust gas pipe enters into the inside of the outside cover 22, and then collides with the inside wall part 211 of the inside cover 21. The flowing direction of the exhaust gas G is clanged along the inside wall part 211. The exhaust gas G further flows through a gap between the inside cover 21 and the outside cover 22 of the protection cover 2, and enters into the inside of the inside cover 21 through the inside introduction holes 214. The exhaust gas G simultaneously flows to the deposition part 13 because the deposition part 13 is arranged to be exposed to the flow of the exhaust gas G.

Next, a description will be given of the action and effects of the particulate matter detection sensor according to the first exemplary embodiment.

The particulate matter detection sensor 1 has the concave collection part 131 having the structure previously described. This structure makes it possible to collect particulate matter which has collided with the deposition part 13 with high efficiency. That is, even if the particulate matter enters into the concave collection part 131, and collides with and rebounds from the inner peripheral surface of the concave collection part 131, it is possible for the rebounded particulate matter to easily collide again with the inner peripheral surface of the concave collection part 131 because the concave collection part 131 is formed to have a depressed shape when viewed from the end surface of the element part 10. A moving speed of the particulate matter is reduced when the particulate matter collides, at the first time, with the inner peripheral surface of the concave collection part 131. The particulate matter is easily attracted to the inner peripheral surface of the concave collection part 131 when the particulate matter collides again with the inner peripheral surface of the concave collection part 131. Accordingly, it is possible for the formation of the concave collection part 131 to increase the collection rate of the deposition part 13.

The particulate matter detection sensor 1 has the protection part 2 which has the inside cover 21 and the outside cover 22. The inside cover 21 covers the deposition part 13 of the element part and the surrounding of the deposition part 13. The introduction holes as through holes are formed in the protection cover 2 so as to introduce exhaust gas. That is, exhaust gas is introduced into the inside of the particulate matter detection sensor 1 through the introduction holes. This structure makes it possible to generate the flowing direction of the introduced exhaust gas to the concave collection part 131. This structure makes it possible to supply the exhaust gas containing particulate matter to the deposition part 13 with high efficiency. Because the introduced exhaust gas is flowing in a unique flowing direction, and the concave collection part 131 is formed along this unique flowing direction of the introduced exhaust gas, the structure of the particulate matter detection sensor 1 has increased collection efficiency.

Further, the particulate matter detection sensor 1 has the structure in which the plural detection electrodes 14 and the plural insulation members 12 which are alternately stacked to form the laminated part 11, and the deposition part 13 and the detection electrodes 14 are formed on the front surface of the laminated part 11. This structure makes it possible to reduce a distance between the detection electrodes 14 and to easily produce the particulate matter detection sensor 1 having an excellent detection sensitivity.

As previously described, the first exemplary embodiment provides the particulate matter detection sensor 1 having increased detection sensitivity to detect particulate matter contained in exhaust gas.

Second Exemplary Embodiment

Figure 5:
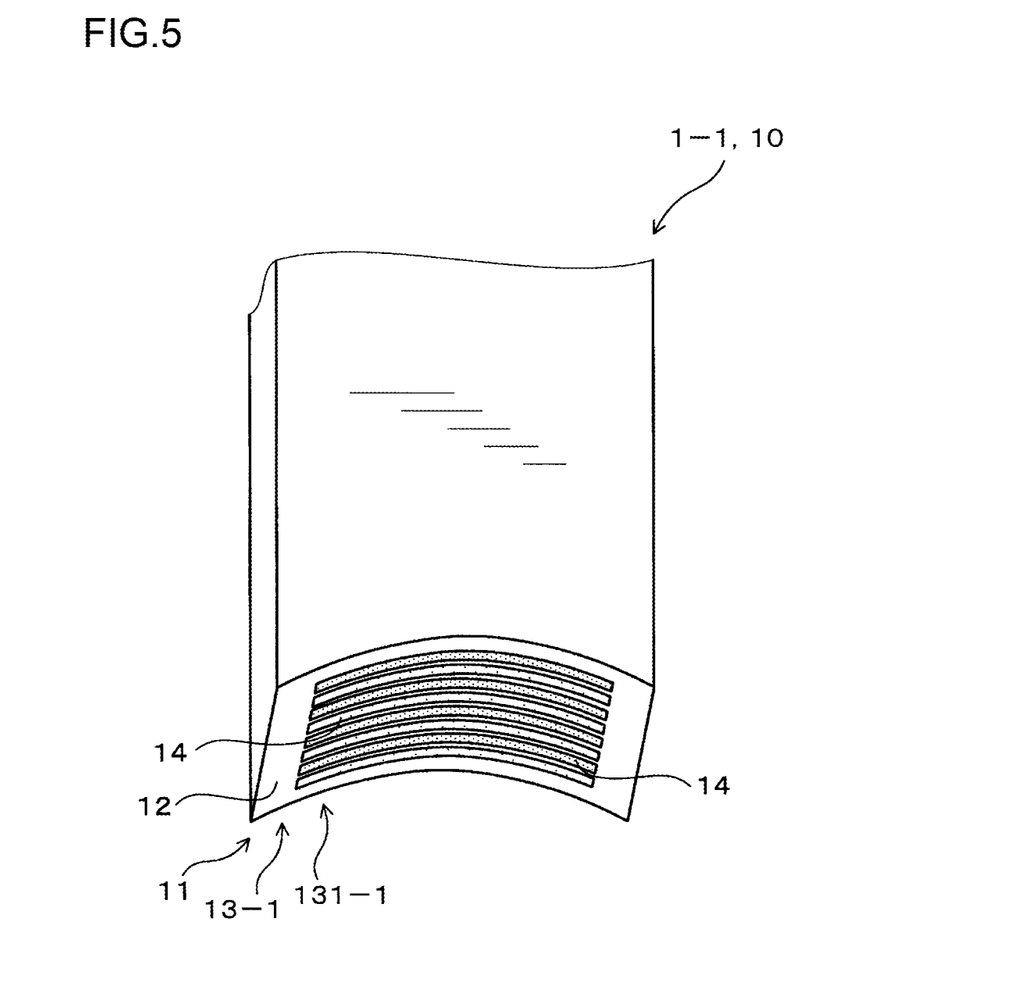
FIG. 5 is a schematic view explaining an element part of a particulate matter detection sensor according to a second exemplary embodiment of the present invention.

A description will be given of the particulate matter detection sensor 1-1 according to the second exemplary embodiment with reference to FIG. 5. As shown in FIG. 5, the particulate matter detection sensor 1-1 according to the second exemplary embodiment has a structure which is a modification of the structure of the particulate matter detection sensor 1 according to the first exemplary embodiment. The particulate matter detection sensor 1-1 has the structure which is different from the structure of the particulate matter detection sensor 1.

In the particulate matter detection sensor 1-1 according to the second exemplary embodiment, a concave collection part 131-1 is formed on a deposition part 13-1.

The concave collection part 131-1 has a curved shape having a bowl shape having an arc-shaped curved surface which is perpendicular to the arrangement of the lamination direction in the laminated part 11.

Other components in the particulate matter detection sensor 1-1 according to the second exemplary embodiment have the same structure of those in the particulate matter detection sensor 1 according to the first exemplary embodiment. The components in the particulate matter detection sensor 1-1 according to the second exemplary embodiment designated by the same reference numbers and characters have the same action and effects of the components designated by the same reference numbers and characters in the particulate matter detection sensor 1 according to the first exemplary embodiment.

The surface of the concave collection part 131-1 has an arc-shape cross section which is perpendicular to the arrangement direction of the pair of the detection electrodes 14. An angle of an inner peripheral surface of the concave collection part 131-1 gradually varies as shown in FIG. 5. This structure makes it possible to collect particles of particulate matter travelling in different directions with high efficiency The same reference numbers and characters used in the explanation of the particulate matter detection sensor 1-1 according to the second exemplary embodiment and in FIG. 5 show the same action and effects of the particulate matter detection sensor 1 according to the first exemplary embodiment.

Third Exemplary Embodiment

Figure 6:
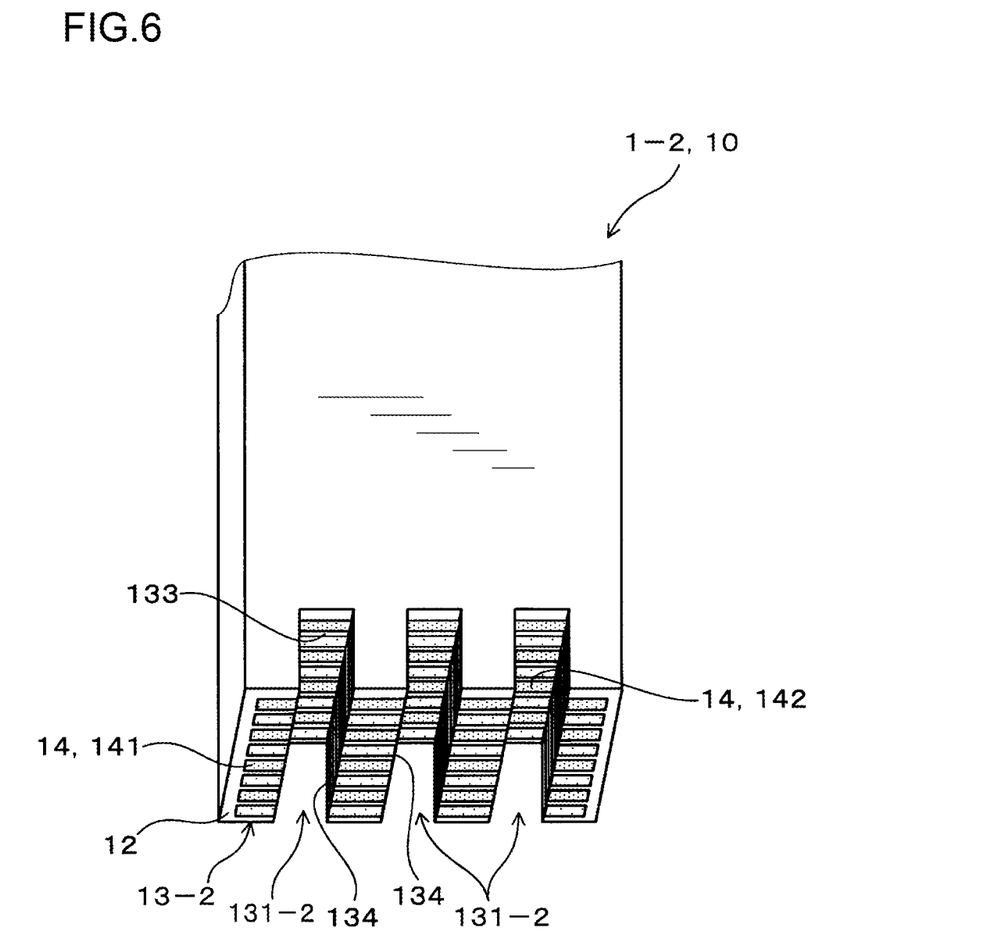
FIG. 6 is a schematic view explaining an element part of a particulate matter detection sensor according to a third exemplary embodiment of the present invention.

A description will be given of the particulate matter detection sensor 1-2 according to the third exemplary embodiment with reference to FIG. 6. As shown in FIG. 6, the particulate matter detection sensor 1-2 according to the third exemplary embodiment has an inner electrode part 142 and an outer electrode part 141. The inner electrode part 142 is formed in the inside of concave collection parts 131-2. The outer electrode part 141 is formed in the collection parts 13-2 excepting in the formation area of the concave collection parts 131-2. In the particulate matter detection sensor 1-2 according to the third exemplary embodiment, the inner electrode part 142 is formed at the inside of the concave collection parts 131-2 formed on the front surface of the element part 10. The inner electrode part 142 is formed on the concave bottom surface 133 of the concave collection parts 131-2 and on each pair of concave side surfaces 134.

In addition, the outer electrode part 141 is formed excepting in the formation area of the concave collection parts 131-2. That is, the outer electrode part 141 is formed on the front surface of the element part 10 between the adjacent concave collection parts 131-2 and formed at the outside of the both ends of the concave collection parts 131-2. The inner electrode part 142 is electrically connected to the outer electrode part 141.

Other components in the particulate matter detection sensor 1-2 according to the third exemplary embodiment have the same structure of those in the particulate matter detection sensor 1 according to the first exemplary embodiment shown.

The components in the particulate matter detection sensor 1-2 according to the third exemplary embodiment shown in FIG. 6 designated by the same reference numbers and characters have the same action and effects of the components designated by the same reference numbers and characters in the particulate matter detection sensor 1 according to the first exemplary embodiment.

The particulate matter detection sensor 1-2 according to the third exemplary embodiment has the structure in which particulate matter contained in exhaust gas is detected at the outside area of the concave collection parts 131-2, and the inner electrode part 142 is formed in the concave collection parts 131-2. This structure makes it possible to provide the increased detection sensitivity of the sensor element 10.

Further, because the plural concave collection parts 131-2 are formed in the deposition part 13-2, this increases the collection rate of collecting particles of particulate matter with high efficiency. For example, the three concave collection parts 131-2 are formed in the structure shown in FIG. 6. The particulate matter detection sensor 1-2 according to the third exemplary embodiment has the same action and effects of the particulate matter detection sensor 1 according to the first exemplary embodiment.

In the particulate matter detection sensors 1, 1-1 and 1-2 according to the first to third exemplary embodiments, the concave collection parts 131, 131-1 and 131-2 have the same cross sectional shape in the lamination direction. For example, it is acceptable for each of the concave collection parts 131, 131-1 and 131-2 to have a cup shape around the central axis of the particulate matter detection sensor 1, 1-1 and 1-2.

In the particulate matter detection sensors 1, 1-1 and 1-2 according to the first to third exemplary embodiments, it is preferable for each of the outside corner parts of the concave collection parts 131, 131-1 and 131-2 and each of the inside corner parts of the concave collection parts 131, 31-1 and 131-2 to have a rounded shape as a rounded surface or a cut surface. For example, when the outside corner part or the inside corner part has a rounded surface, it is possible for the rounded part to have a range of R0.01 to R1.0 (i.e. has the rounded surface within a range of 0.01 mm to 1.0 mm). For example, when the outside corner part or the inside corner part has a cut surface, it is possible for this cut surface to have within a range of C0.01 to C1.0 (i.e. the cut dimension within a range of 0.01 mm to 1.0 mm. This structure makes it possible to improve the resistance to a stress applied due to a collision or a rapid temperature change. It is more preferable to perform such a rounding process or a cutting process so as to suppress occurrence of breaking and defects during the firing process.

Comparative Experiment

The comparative experiment performed a comparison in detection sensitivity between the particulate matter detection sensors 1, 1-1 and 1-2 according to the first to third exemplary embodiments and comparative example of a conventional particulate matter detection sensor having a conventional structure without any concave collection parts 131, 131-1 and 131-2.

This conventional particulate matter detection sensor has the structure of the particulate matter detection sensor without the formation of the concave collection part 131. That is, the conventional particulate matter detection sensor has the structure in which the collection part has a surface which is perpendicular to the axial direction of the particulate matter detection sensor. Other components of the conventional particulate matter detection sensor have the same of those components in the particulate matter detection sensor according to the first exemplary embodiment.

The comparison experiment detected a dead mass of particulate matter when exhaust gas has a temperature of 200° C., and a concentration of particulate matter contained in the exhaust gas is 3 mg/m$^3$, and the exhaust gas has a flow speed of 20 m/s and 50 m/s. The dead mass of particulate matter represents a total mass of particulate matter discharged during a period until an output signal of the particulate matter detection sensor has varied.

TABLE 1

| | Dead mass of particulate matter | |
|---|---|---|
| | Flow speed of 20 m/s | Flow speed of 50 m/s |
| Comparative example | 34 mg | 52 mg |
| First exemplary embodiment | 28 mg | 35 mg |
| Second exemplary embodiment | 26 mg | 32 mg |
| Third exemplary embodiment | 25 mg | 29 mg |

Table 1 shows the results of the comparison experiment. In Table 1, the comparative example has a dead mass of particulate matter of 34 mg when the exhaust gas has a flow speed of 20 m/s, and a dead mass of particulate matter of 52 mg, apparently when exhaust gas has the flow speed of 50 m/s.

In Table 1, the particulate matter detection sensor 1 according to the first exemplary embodiment has a dead mass of particulate matter of 28 mg when the flow speed of exhaust gas is 20 m/s, and a dead mass of particulate matter is 28 mg when the flow speed of exhaust gas is 20 m/s, and a dead mass of particulate matter of 35 mg when the flow speed of exhaust gas is 50 m/s.

The experimental results show that the dead mass of particulate matter of the particulate matter detection sensor 1 according to the first exemplary embodiment becomes smaller than the dead mass of particulate matter of the conventional particulate matter detection sensor according to the comparative example.

In addition, the experimental results show that a variation of the dead mass of particulate matter of the particulate matter detection sensor 1 according to the first exemplary embodiment is smaller than a variation of the dead mass of particulate matter of the conventional particulate matter detection sensor according to the comparative example when the flow speed of exhaust gas is changed.

This structure of the particulate matter detection sensor 1 according to the first exemplary embodiment makes it possible to prevent particulate matter from being rebounded in the collection part 13 even if the flow speed of exhaust increases, and to increase the collection efficiency of collecting particulate matter contained in exhaust gas.

Further, it can be recognized from the detection results shown in Table 1 that the dead mass of particulate matter of the particulate matter detection sensor 1-1 according to the second exemplary embodiment is smaller than that of the particulate matter detection sensor 1 according to the first exemplary embodiment, and the dead mass of particulate matter of the particulate matter detection sensor 1-2 according to the third exemplary embodiment is even smaller than that of the particulate matter detection sensor 1-1 according to the second exemplary embodiment. This trend regarding the dead mass of particulate matter does not vary in both cases having the exhaust gas flow speed of 20 m/s and the exhaust gas flow speed of 50 m/s.

Still further, it can be recognized from the detection results shown in Table 1 that the particulate matter detection sensor 1-1 according to the second exemplary embodiment is smaller in change amount of the dead mass of particulate matter than particulate matter detection sensor 1 according to the first exemplary embodiment, and the particulate matter detection sensor 1-2 according to the third exemplary embodiment is even smaller in change amount of the dead mass of particulate matter than the particulate matter detection sensor 1-1 according to the second exemplary embodiment.

The detection results previously described clearly show that the particulate matter detection sensors 1, 1-1 and 1-2 according to the first to third exemplary embodiments have an excellent detection sensitivity when compared with the detection sensitivity of the particulate matter detection sensor having a conventional structure. Further, the detection results previously described clearly show that the particulate matter detection sensor 1-1 according to the second exemplary embodiment has the detection sensitivity which is higher than the detection sensitivity of the particulate matter detection sensor 1 according to the first exemplary embodiment. Still further, the detection results previously described clearly show that the particulate matter detection sensor 1-2 according to the third exemplary embodiment has the detection sensitivity which is higher than the detection sensitivity of the particulate matter detection sensor 1-1 according to the second exemplary embodiment.

REFERENCE SIGNS LIST

1, 1-1, 1-2 Particulate matter detection sensor, 10 Element part, 13, 13-1, 13-2 Deposition part, 131, 131-1, 131-2 Concave collection part, and 14 Detection electrodes.

The invention claimed is:
1. A particulate matter detection sensor comprising:
   an element part capable of detecting an amount of particulate matter contained in exhaust gas emitted from an internal combustion engine;
   a deposition part formed in the element part capable of collecting some of the particulate matter contained in exhaust gas; and
   at least a pair of detection electrodes formed on the deposition part, the pair of detection electrodes facing with each other at a predetermined interval,
   wherein the particulate matter detection sensor is configured to change an output electrical signal due to electrical properties between the pair of the detection electrodes when the particulate matter are deposited on the deposition part,
   the deposition part comprises a concave collection part formed in a concave shape, the concave collection part comprises a pair of a first detection surface and a second detection surface arranged adjacently with each other in an adjacent direction which is perpendicular to a depth direction of the concave collection part, and a component of a normal vector of each of the first detection surface and the second direction surface in the adjacent direction is in a reverse direction with each other,
   when observed from the depth direction of the concave collection part, each of the pair of detection electrodes extends from the first detection surface toward the second detection surface along the adjacent direction, and
   the pair of detection electrodes are arranged to face with each other in an orthogonal direction which is perpendicular to the adjacent direction and the depth direction.
2. The particulate matter detection sensor according to claim 1, wherein each of the first detection surface and the second detection surface is formed in a plate shape, and crosses with each other at a predetermined angle.

3. The particulate matter detection sensor according to claim 1, wherein first detection surface and the second detection surface are connected together and to form an arc-shaped curved surface.

4. The particulate matter detection sensor according to claim 1, wherein each of the first detection surface and the second detection surface is formed in a plate shape, and is arranged at right angles to each other in the adjacent direction.

5. A particulate matter detection sensor comprising an element part capable of detecting an amount of particulate matter contained in exhaust gas emitted from an internal combustion engine, wherein
 a deposition part and at least a pair of detection electrodes are formed on at least one surface of the element part, the deposition part collecting some of the particulate matter contained in exhaust gas, and the pair of the detection electrodes are arranged on the deposition part, and
 the particulate matter detection sensor generates and transmits an output electrical signal which is changed due to electrical properties between the pair of the detection electrodes, the electrical properties between the pair of the detection electrodes varying due to the amount of particulate matter deposited on the deposition part,
 a concave collection part is formed in the deposition part, and the concave collection part has a concave shape when viewed from the one surface of the element part; and
 a laminated part in which a plurality of the detection electrodes and a plurality of lamination members being electrically insulating are alternately stacked, wherein the deposition part and the plurality of the detection electrodes are formed on an edge surface of the laminated part.

6. The particulate matter detection sensor according to claim 5, wherein the pair of the detection electrodes comprises an outer electrode part and an inner electrode part, the inner electrode part is formed inside of the concave collection part, and the outer electrode part is formed in the collection part but outside the concave collection part, and the outer electrode part are the inner electrode part are electrically connected with each other.

7. The particulate matter detection sensor according to claim 5, further comprising a protection cover with which the deposition part is covered, wherein introduction holes are formed in the protection cover so as to introduce exhaust gas into the protection cover and to generate flow of the introduced exhaust gas to the deposition part.

8. The particulate matter detection sensor according to claim 5, wherein the concave collection part has a bowl shape having an arc-shaped curved surface.

9. The particulate matter detection sensor according to claim 5, wherein the concave collection part formed in the collection part comprises plural concave collection parts.

* * * * *